United States Patent [19]

Zilbershtein

[11] Patent Number: 5,392,772
[45] Date of Patent: Feb. 28, 1995

[54] ENDOTRACHEAL TUBE SET FOR ANESTHESIA HAVING A VALVE AND VALVE POSITION INDICATOR FOR SINGLE OR DOUBLE LUNG VENTILATION

[76] Inventor: Michael Zilbershtein, 3 Trescott Path, Fort Salonga, N.Y. 11768

[21] Appl. No.: 57,626

[22] Filed: May 7, 1993

[51] Int. Cl.$^6$ .......................... A62B 9/02; A62B 9/06; A61M 16/00; F16K 37/00
[52] U.S. Cl. .......................... 128/205.24; 128/207.16; 137/556; 137/625.47
[58] Field of Search ...................... 128/205.24, 207.14, 128/207.15, 207.16, 207.18, 911, 912, DIG. 26; 137/556, 556.3, 556.6, 625.47

[56] References Cited

U.S. PATENT DOCUMENTS

| | | | |
|---|---|---|---|
| 2,791,217 | 5/1957 | Iskander | 128/205.24 |
| 3,276,472 | 10/1966 | Jinkens et al. | 137/556 |
| 3,485,265 | 12/1969 | Buono | 137/156.6 |
| 3,750,704 | 8/1973 | Burke et al. | 137/625.47 |
| 3,774,604 | 11/1973 | Danielsson | 137/625.47 |
| 4,219,021 | 8/1980 | Fink | 137/556.6 |
| 4,489,721 | 12/1984 | Ozaki et al. | 128/205.24 |
| 4,494,565 | 1/1985 | Sinclair et al. | 137/556 |
| 4,593,717 | 6/1986 | Levasseur | 137/556.6 |
| 4,674,496 | 6/1987 | Svadjian et al. | 128/207.16 |
| 5,040,532 | 8/1991 | Alfery | 128/207.16 |
| 5,135,026 | 8/1992 | Manska | 137/556 |

*Primary Examiner*—Kimberly L. Asher
*Attorney, Agent, or Firm*—I. Zborovsky

[57] ABSTRACT

An endotracheal tube with two lumens is connected with an anesthesia machine by a connector having an outer element with two pairs of passages connected with the tube and the machine correspondingly, and an inner element turnable in the outer element to connect all passages with each other so as to ventilate both lungs, or to connect one passage or another passage of the first pair with one passage or another passage of the second pair to ventilate one or another lung.

8 Claims, 2 Drawing Sheets

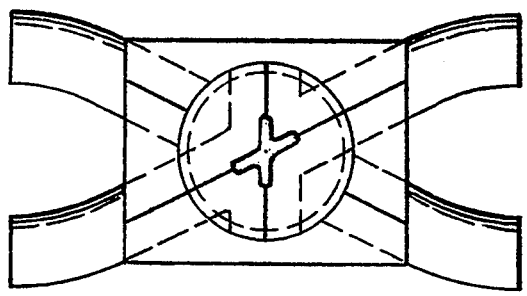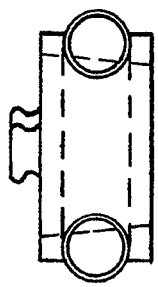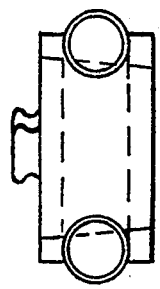
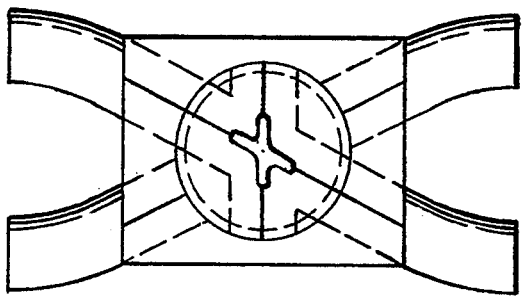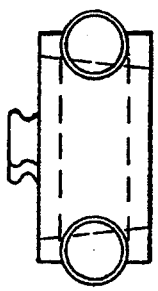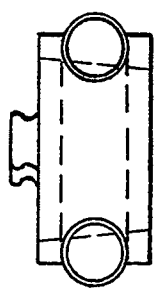
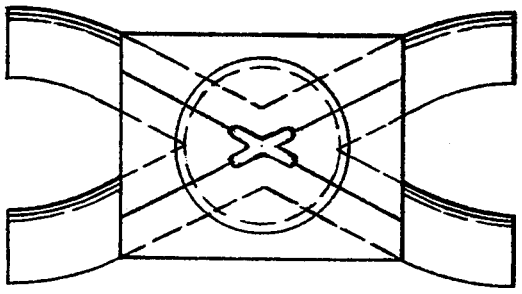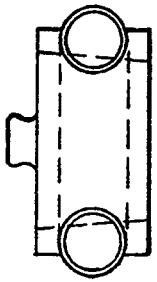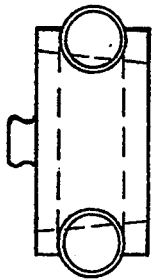
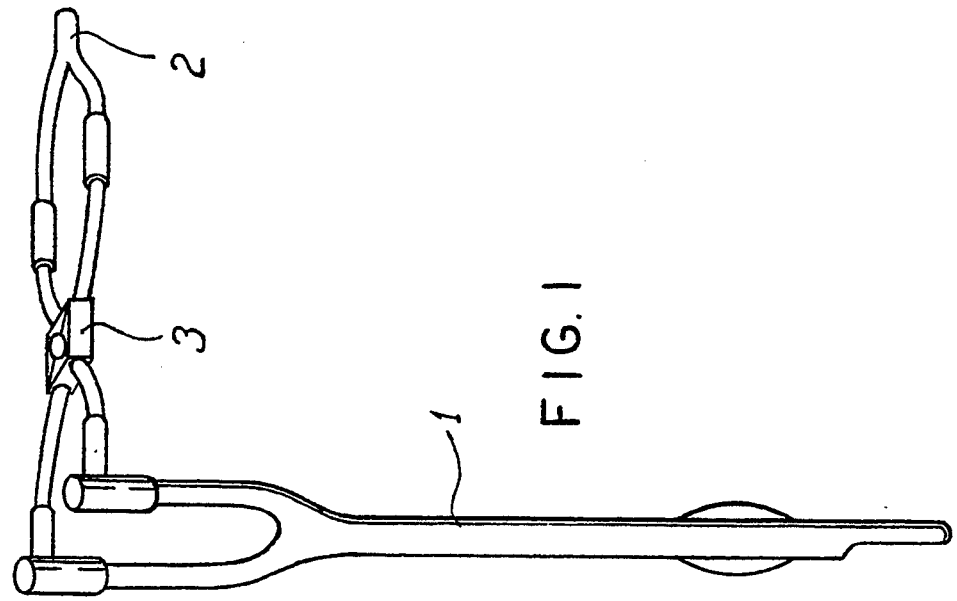

ENDOTRACHEAL TUBE SET FOR ANESTHESIA HAVING A VALVE AND VALVE POSITION INDICATOR FOR SINGLE OR DOUBLE LUNG VENTILATION

BACKGROUND OF THE INVENTION

The present invention relates to a device for ventilating lungs from an anesthesia machine through double-lumen endotracheal tube, and to a connector for it.

There are several endotracheal tubes in production, which are used with adaptors or connectors. However, all connectors possess the same drawbacks. In order to provide only one lung ventilation, the passage from the anesthesia machine to the lung to be operated has to be closed. A special instrument, such as a clamp is required for the closing of the passage, and the maneuver of this kind is technically inconvenient and time consuming. Some devices have been proposed to avoid this inconvenience. One of such devices is introduced by H. Andersen et al. (see "Anesthesiology", 56-54,1982). The connector of this device has, however, a relatively large size and is heavy, and therefore is cumbersome and awkward for practical use. This device also increases the cost of the double-lumen endotracheal tube set.

SUMMARY OF THE INVENTION

Accordingly, it is an object of the present invention to provide a device for ventilating lungs from an ansthesia machine, and a connector therefor, which avoids the disadvantages of the prior art.

More particularly, it is an object of the present invention to provide such a device of the above mentioned type, which is simple, small and light and does not substantially increase the cost.

In keeping with these objects and with others which will become apparent hereinafter, one features of the present invention resides, briefly stated, in a connector which has an outer hollow element with an inner opening and a wall having two first passages connectable with a double lumen endotracheal tube and the inner opening and two second passages connected with the inner opening and connectable with an anasthesia machine, and an inner element turnable in the outer element and having intersecting passages adapted to connect all passages with one another to ventilate both lungs, or one or another first passage with one or another second passage to ventilate a left lung or a right lung.

The novel features of the present invention are set forth in the appended claims. The invention itself, however, will be best understood from the following description of preferred embodiments, which is acompanied by the following drawings.

BRIEF DESCRIPTION OF THE DRAWINGS

FIG. 1 is a view schematically showing a device in accordance with the present invention;

FIGS. 2a-2c are side views of a connectors of the inventive devices in three different position;

FIGS. 3a-3c and 4a-4c are views from above and views from below of the connector of FIGS. 2a-2c in corresponding three position;

DESCRIPTION OF PREFERRED EMBODIMENTS

A device for ventilating lungs in accordance with the present invention includes a double-lumen endotracheal tube 1 which is connected with a tube 2 extending from a not shown anesthesia machine through an inventive connector 3 which will be explained hereinbelow.

Figure 6A:
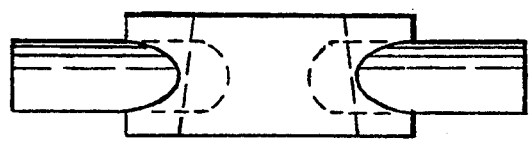
FIGS. 5 and 6 are views showing two modifications of an outer hollow member of the connector.
Figure 6:
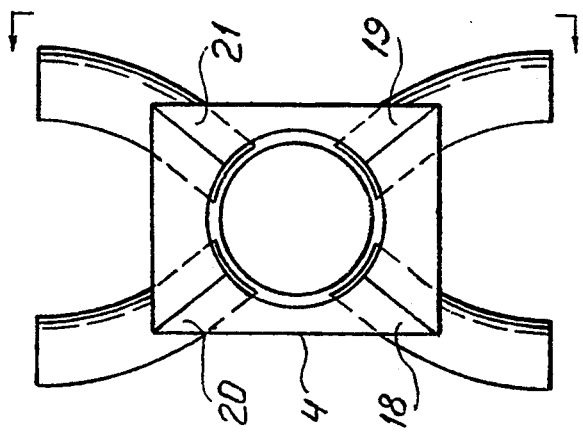
Figure 5A:
Figure 5:
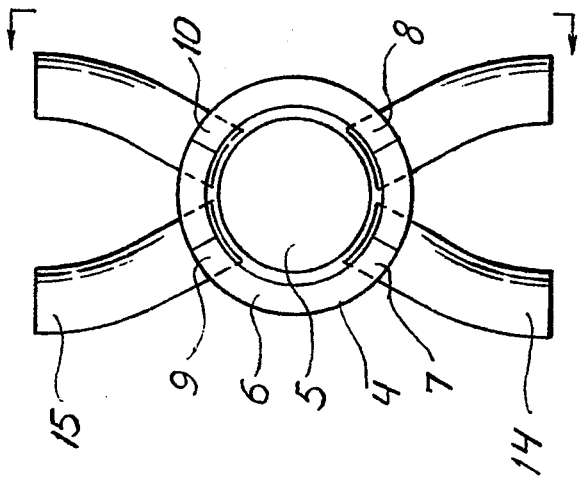
Figure 7A:
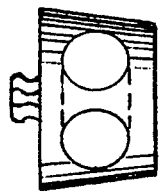
FIG. 7 is a view showing an inner member of the connector in accordance with the present invention.
Figure 7:
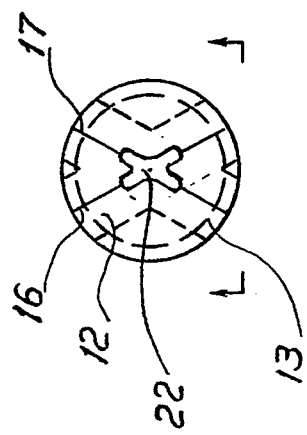

The connector 3 has an outer hollow element 4 which can be cylindrical as shown in FIG. 4 or rectangular as shown in FIG. 5, or of another shape. The outer element 4 has a single central inner opening 5 which is limited by a wall 6 provided with two first passages 7 and 8 and two second passages 9 and 10 which communicate the inner opening 5 with an outer side of the element 4. The passages are located diametrically opposite to one another and continuations of their axes intersect one another. As can be seen from the drawings, the passages 9 and 8 are located on one diameter and their axes coincide with one another, while the passages 10 and 7 are also located on the same another diameter and their axes coincide with one another. The connector further has an inner element 11 which is turnably received in the inner opening 5 of the outer element and has two intersecting and communicating channels 12 and 13. Connecting tubes 14 connect the passages 7 and 8 with two lumens of the endotracheal tube 1, while further connecting tubes 15 connect the passages 9 and 10 with the anesthesia machine.

The inner element 11 is turnable between 3 positions in the outer element 4. In one position shown in FIGS. 2a, 3a, 4a the outer openings of the intersecting channels and 13 coincide with inner openings of the passages 7,8 and 9,10 and thereby the passages 7,8 are connected with the passages 9,10 so that when a ventilating medium is supplied from the ansthesia machine to the connector, it flows through the connector 3 into both lumens of the tube 1 and ventilates both lungs. In the position shown in FIGS. 2b, 3b, 4b the passage 10 communicates with the passage 7 while the passage 9 and the passage 8 do not communicate, so that the ventilating medium is supplied only to one lumen of the tube 1 and ventilates only one lung. Finally, in the position shown in FIGS. 2c, 3c, 4c the passage 9 communicates with the passage 8 while the passages 10 and 7 do not communicate with one another, so that the ventilating medium is supplied only to another lumen of the tube 1 and ventilates only another lung.

In order to easily obtain the desired angular position of the inner element relative to the outer element and therefore the desired one- or two lung ventilation,lines 16 and 17 which represent projections of axes of the intersecting channels 12 and 13 are arranged on the end side of the inner member 11, while the end side of the outer member 4 have diagonal lines 18,19,20,21 substantially representing projections of axes of the passages 7,8,9,10. By coinciding of the lines 16 and 17 either with all lines 18,19,20,21 or with only one pair of the later mentioned lines, a corresponding angular position of the inner element relative to the outer element and ventilating of both lungs or of only one corresponding lung can be determined.

As can be seen from the drawings, the outer surface of the inner element 11 and the inner surface of the outer element 4 are conical, to facilitate holding of one element in the other element. However, these surfaces can be also cylindrical.

The end side of the inner element 11 is provided with a single handle 22 located centrally and easily graspable by a user to turn the inner element. The handle is formed by two intersecting portions, which facilitate grasping of the handle and additionally identify the angular position of the inner element 11 relative to the outer element 4 and therefore ventilation of corresponding one lung or both lungs.

The invention is not limited to the details shown since various modifications and structural changes are possible without departing in any way from the spirit of the invention.

What is desired to be protected by Letters Patent is set forth in the appended claims.

I claim:

1. A connector for connecting a double-lumen endotracheal tube to an anesthesia machine and for selectively ventilating one or both lungs of a patient comprising an outer hollow element having a central axis, a single inner opening and a wall provided with first two passages connectable with a double-lumen endotracheal tube and communicating with said inner opening and second two passages connectable with an anesthesia machine and also communicating with said inner opening; and a single inner element rotatably positioned in said single inner opening of said outer hollow element and having two intersecting channels formed therein means for rotating said inner element between three angular positions, a first angular position having said channels connect said first two passages with said second two passages wherein ventilating medium can be supplied from the anesthesia machine through the connector to ventilate both lungs, a second angular position having only one of said first passages connected with only one of said second passages wherein the ventilating medium can be supplied through the connector to ventilate only one lung, and a third angular position having the other of said two passages connected with the other of said second passages wherein the ventilating medium can be supplied through the connector to ventilate the other lung, said first passages and said second passages being located diametrically opposite to one another.

2. A connector as defined in claim 1, and further comprising first two connecting tubes connected with said first two passages and connectable with the anesthesia machine, and second two connecting tubes connected with said second two passages and connectable with the double-lumen endotracheal tube.

3. A connector as defined in claim 1, wherein said inner opening of said outer hollow element is cylindrical, said inner element having a cylindrical outer surface.

4. A connector as defined in claim 1, wherein said inner opening of said outer hollow element is conical, said inner element having a conical outer surface corresponding to said conical inner opening.

5. A connector as defined in claim 1, wherein said inner element has an end side; and said means for rotating said inner element comprises a single handle arranged on said end side of said inner member substantially in a center of the latter for turning said inner element.

6. A connector as defined in claim 5, wherein said handle has two intersecting parts providing said handle with X-shape on an end view.

7. A connector as defined in claim 1, wherein said inner element has means for identification of the angular position of said inner element positioned on said means for rotating said inner element, said means for identification comprising an end side provided with two intersecting lines arranged along projections of axes of said two intersecting channels.

8. A device for ventilating the lungs of a patient by an anesthesia machine, comprising a double-lumen endotracheal tube having two lumens through which a ventilating medium is supplied to a patient's lungs when said tube is introduced into a patient; and a connector having an outer hollow element having a central, a single inner opening and a wall provided with first two passages connected to said two lumens of said tube and communicating with said inner opening and second two passages connected to an anesthesia machine, and a single inner element located in said single inner opening and having two intersecting channels formed therein means for rotating said inner element between three angular positions, a first angular position having said channels connect said first two passages with said second two passages wherein ventilating medium can be supplied from the anesthesia machine through said connector to ventilate both lungs, a second angular position having only one of said first passages connected with only one of said second passages wherein the ventilating medium can be supplied through said connector to ventilate only one lung, and a third angular position having the other of said first passages connected with the other of said second passages wherein the ventilating medium can be supplied to the other lung, said first passages and said second passages being located diametrically opposite to one another.

* * * * *